United States Patent [19]

Davis

[11] Patent Number: 5,277,136
[45] Date of Patent: Jan. 11, 1994

[54] PROCESSING FACILITY FOR DISPOSING OF INFECTIOUS MEDICAL WASTES

[75] Inventor: Robert S. Davis, Boston, Mass.

[73] Assignee: BioSafe Inc., Cambridge, Mass.

[21] Appl. No.: 763,135

[22] Filed: Sep. 20, 1991

[51] Int. Cl.$^5$ .......................... F23G 5/00; F27B 7/08
[52] U.S. Cl. .................................... 110/347; 110/110; 110/222
[58] Field of Search ............... 110/222, 228, 110, 255, 110/275, 276

[56] References Cited

U.S. PATENT DOCUMENTS

| | | | |
|---|---|---|---|
| 2,932,712 | 4/1960 | Levin | 110/110 |
| 4,121,524 | 10/1978 | Voelskow et al. | 110/222 |
| 4,270,470 | 6/1981 | Barnett et al. | 110/222 |
| 4,504,222 | 3/1985 | Christian | 110/110 |
| 4,628,828 | 12/1986 | Holtham et al. | 110/222 |
| 4,750,437 | 6/1988 | Rouse | 110/222 |
| 4,784,603 | 11/1988 | Robak, Jr. et al. | 110/222 |
| 4,993,943 | 2/1991 | Norris et al. | 110/347 |
| 4,995,324 | 2/1991 | Williams | 110/222 |

FOREIGN PATENT DOCUMENTS 3604582.9  2/1986  Fed. Rep. of Germany.

Primary Examiner—Henry C. Yuen
Attorney, Agent, or Firm—Fish & Richardson

[57] ABSTRACT

A method for disposing of infectious medical waste in a closed system includes the steps of shredding the waste in the closed system to reduce the waste to small particles and indirectly heating the waste particles in the closed system by contacting the waste particles with a heated surface. The waste particles are indirectly heated to a sufficiently high temperature and for a sufficient period of time to produce a quantitative assurance of sterilization of the waste particles. Air is continuously drawn through the closed system to control the pressure and moisture in the closed system.

22 Claims, 4 Drawing Sheets

PROCESSING FACILITY FOR DISPOSING OF INFECTIOUS MEDICAL WASTES

BACKGROUND OF THE INVENTION

The present invention relates to systems and processes for the environmentally safe disposal of infectious medical waste.

The safe disposal of infectious medical waste has become a major environmental and public safety concern in recent years. Public safety concerns include the spread of disease by the indiscriminate disposal of infectious medical waste in municipal landfills, or by dumping at sea. A major environmental danger concerns many substandard medical waste incinerators operated at hospitals across the United States. Usually concentrated in populous urban areas, these facilities each year emit tons of toxins into the atmosphere, including dioxins, furans, heavy metals, and acid gases. The current state of medical waste disposal in the United States is chronicled by Hershkowitz, Alan, "Without a Trace: Handling Medical Waste Safely", *MIT Technology Review*, August/September 1990, incorporated herein by reference.

Under current U.S. Environmental Protection Agency (EPA) rules, medical waste must be both treated to substantially remove or reduce any biological hazard and destroyed so that it is no longer generally recognizable as medical waste. After the waste has been treated and destroyed in this way, the EPA does not require it to be tracked and it may be disposed of in the same manner as ordinary garbage.

SUMMARY OF THE INVENTION

In general, in one aspect, this invention features a method for disposing of infectious medical waste in a closed system where the steps of the method include shredding the waste in the closed system to reduce the waste to small particles and indirectly heating the waste particles in the closed system by contacting the waste particles with a heated surface. The indirect heating is to a sufficiently high temperature and for a sufficient period of time to produce a quantitative assurance of sterilization of the waste particles. Also, air is continuously drawn through the closed system to control the pressure and moisture in the closed system. In general, the method does not require the addition of any liquid.

In a further aspect, the method comprises shredding the waste into particles with no dimension greater than approximately one inch and indirectly heating the waste particles to at least 220 degrees Fahrenheit.

In another aspect, the step of indirectly heating the waste comprises transporting the waste particles from one end of a hollow screw conveyor to the other end, where the hollow screw conveyor has an outside surface and is adapted to accept a heat conducting medium inside the hollow section such that the heat conducting medium heats the outside surface and thereby the waste particles contacting the outside surface are heated indirectly by the heat conducting medium.

Additionally, the indirect heating step can utilize a pair of the hollow screw conveyors which are interleaved and counter-rotatable.

In a further aspect, the heat conducting medium comprises heated oil, a heated gas, steam, saturated steam or superheated steam.

In still another aspect, the method includes the step of filtering the continuously drawn air before it is discharged into the atmosphere. Also, the filtering step comprises filtering with both an activated carbon filter to remove volatile organics from the air, and a high efficiency particulate air (HEPA) filter to remove submicron particles, including bacteria, from the air.

DESCRIPTION OF THE PREFERRED EMBODIMENTS

Figure 1:
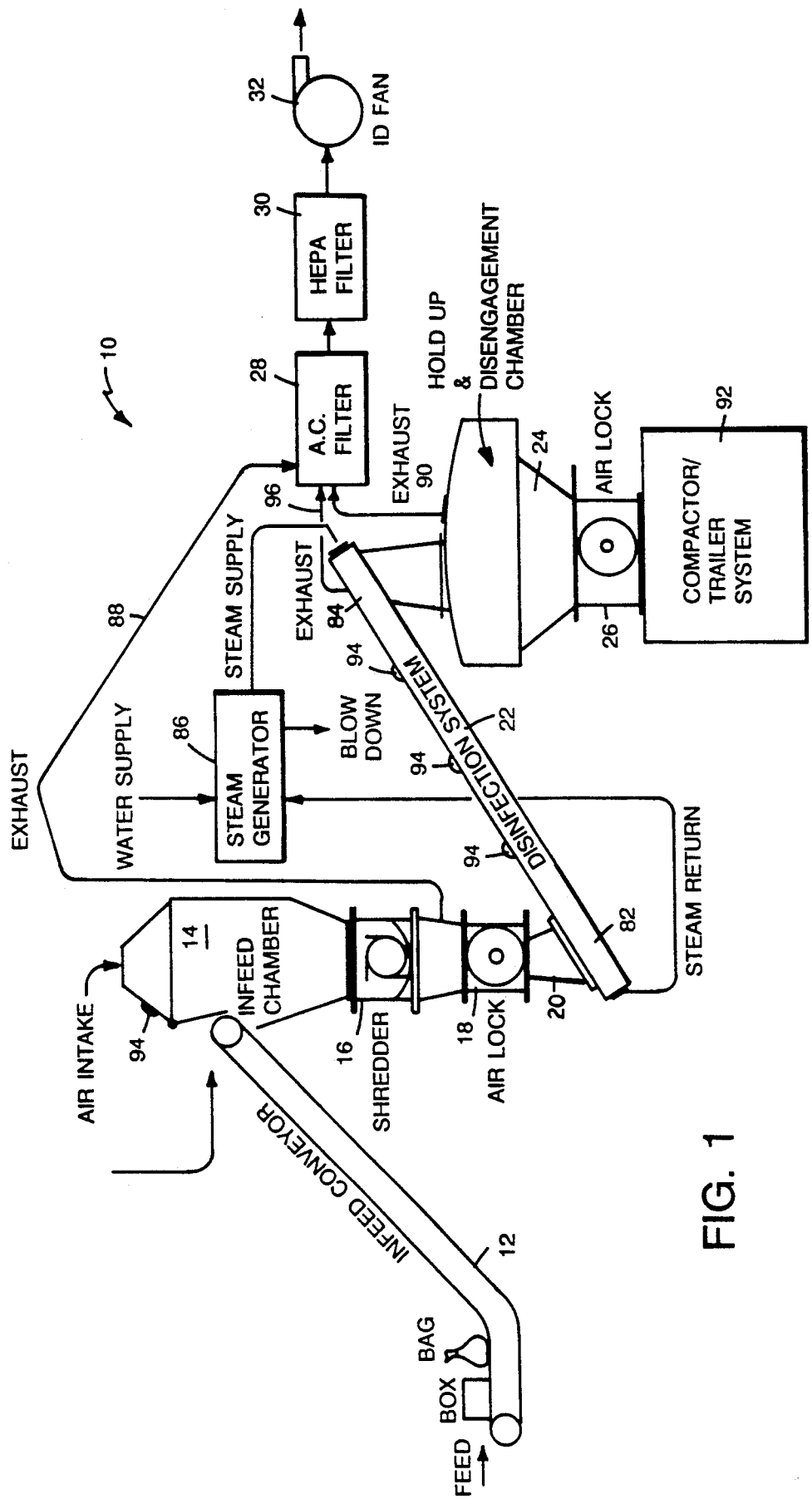
FIG. 1 is a schematic diagram of an embodiment of a closed system and a process for the environmentally safe disposal of infectious medical waste.

Referring to FIG. 1, an embodiment of a closed system 10 for the environmentally safe disposal of infectious medical waste includes an infeed conveyor 12, an infeed chamber 14, a shredder section 16, a rotary air lock 18, an enclosed hopper 20, a disinfection system 22, a hold-up and disengagement chamber 24, another rotary air lock 26, a dual filtration system 28, 30, and a fan 32.

First and second stage shredders for "destroying" the waste are contained in infeed chamber 14 and shredder section 16, respectively. Suitable shredders include 50 HP low speed shear shredders such as those commercially available from Shredding Systems, Inc. (Wilsonville, Oreg.) and Shred Pax Corp. (Wooddale, Ill.).

Disinfection system 22 contains one to four interleaved counter-rotatable hollow screw conveyors. A source of heat is passed through the hollow portion of the screw conveyors to indirectly heat and thereby "treat" the shredded waste passing over the screw conveyors. Suitable indirect-heat-exchanging hollow screw conveyors include the (preferred) commercially-available Holo-Flite ® Processor from Denver Equipment Co. (Colorado Springs, Colo.) and the commercially-available Porcupine Processor from Bethlehem Corp. Similar equipment is also commercially available from Therm-A-Core, Inc. (Fremont, Calif.).

The dual filtration system consists of an activated carbon filter 28 for removing any volatile organics in the air followed by a high efficiency particulate air (HEPA) filter 30 for removing any submicron particles, including bacteria, from the air. Suitable activated carbon and HEPA filters are available from the Cambridge Filter Corp. (Syracuse, N.Y.). Air lock 18 prevents water vapor and air from traveling back through the system and out of infeed chamber 14. Similarly, air or water vapor lock 26 prevents air in the system from escaping. Air locks 18 and 26 are both gas-solid separating devices that act as pressure seals. That is the air locks allow waste to pass but they do not allow air or water vapor to pass.

Closed system 10 is capable of processing (i.e., destroying and treating) from 100 to 6000 pounds of waste per hour. During normal operation, the closed system usually will be required to treat and destroy from 2000 to 2500 pounds of waste per hour. The actual speed of operation of the closed system is determined, in part, by the composition of the waste. The amount of heat input required in the closed system per pound of waste processed ranges from approximately 100 to 400 btu, depending on the moisture content of the waste. The closed system is made from rugged industrial grade equipment and therefore it can operate approximately 8,000 hours per year when properly maintained.

The meaning of "treatment" and "destruction" of medical waste, as used previously and throughout this specification, is taken from Environmental Protection Agency (EPA), Office of Solid State Waste, Standards for the Tracking and Management of Medical Waste (ref: 40 C.F.R. §259). Specifically, "treatment" is defined as a process by which the concentration of microorganisms capable of causing disease in humans is reduced so as to render the Waste noninfectious or less infectious (but not necessarily absolutely sterile) and thus, it is safe to handle, transport, and dispose o the waste. "Destruction" is defined as ruining, tearing apart, or mutilating the waste so that it is no longer recognizable as medical waste.

While it is not necessary to achieve absolute sterility to comply with the EPA rules just mentioned, it is helpful to provide an accepted definition of sterility. Such a definition is provided by Favero, M. S. and Bond, W. W., "Sterilization, Disinfection, and Antisepsis in the Hospital", Chapter 24, p. 185, *Manual of Clinical Microbiology: Fifth Edition*, American Society for Microbiology, Washington, D.C., incorporated herein by reference. Favero and Bond define sterilization as the state in which the probability of any one of a high number e.g., $10^6$ to $10^7$) of dried bacterial endospores surviving is $10^{-6}$ or lower. This definition produces a great degree of overkill as well as a quantitative assurance of sterilization.

Still referring to FIG. 1, "red bag" waste (i.e., infectious waste from hospitals, medical laboratories, doctors' offices, and other sources) is placed on infeed conveyor 12 and enters infeed chamber 14 of the closed system 10. The red bag waste can be either boxed or bagged. The infeed conveyor can be operated continuously to provide a steady stream of waste to the infeed chamber. Upon entering the infeed chamber, the waste encounters the first of two shredders that are in series. The first shredder reduces the waste down to pieces of approximately six to twelve inches and the second shredder reduces these pieces to particles with dimensions less than approximately one inch.

The small particles of waste then pass through the rotary air lock 18 (i.e., a pressure seal) to the enclosed hopper 20 which feeds into the disinfection system 22. The small particles of waste are transported from an inlet end 82 of the disinfection system to an outlet end 84 by the two indirect-heat-exchanging interleaved counter-rotatable hollow screw conveyors. Steam, supplied by a steam generator 86, is circulated within each of the hollow screws and the waste particles are thereby indirectly heated as they are transported from end 82 to end 84. That is, the waste particles are not directly heated by the steam itself but by the transfer of heat from the inside of the screw conveyors to the outside surface that contacts and transports the waste particles. The waste particles do not become "soaked" by the steam because they contact only the outside heated surface of the hollow screw conveyor.

It has been shown by Rutala et al., "Decontamination of Laboratory Microbiological Waste by Steam Sterilization", *Applied and Environmental Microbiology*, June 1982, pp. 1311-1316, incorporated herein by reference, that it is more effective to process smaller batches of waste than larger batches. Also, reducing the waste to small particles increases the surface area of the waste and allows maximum transfer of heat to the waste.

The waste particles in the disinfection system 22 will typically be heated to a temperature in the range 212° to 300° F., with 250° F. being preferred. The heating medium (oil or steam) circulated through the hollow screw conveyors is typically in the range of 212° to 400° F., with 340° to 380° F. being preferred. The total transit time for the particles to go from end 82 to end 84 of the disinfection system 22 (i.e., the residence time of a waste particle in the disinfection system) can range from only a few seconds to several hours, with the 26 seconds to one hour being typical and 30 minutes to 60 minutes being preferred.

Figure 2:
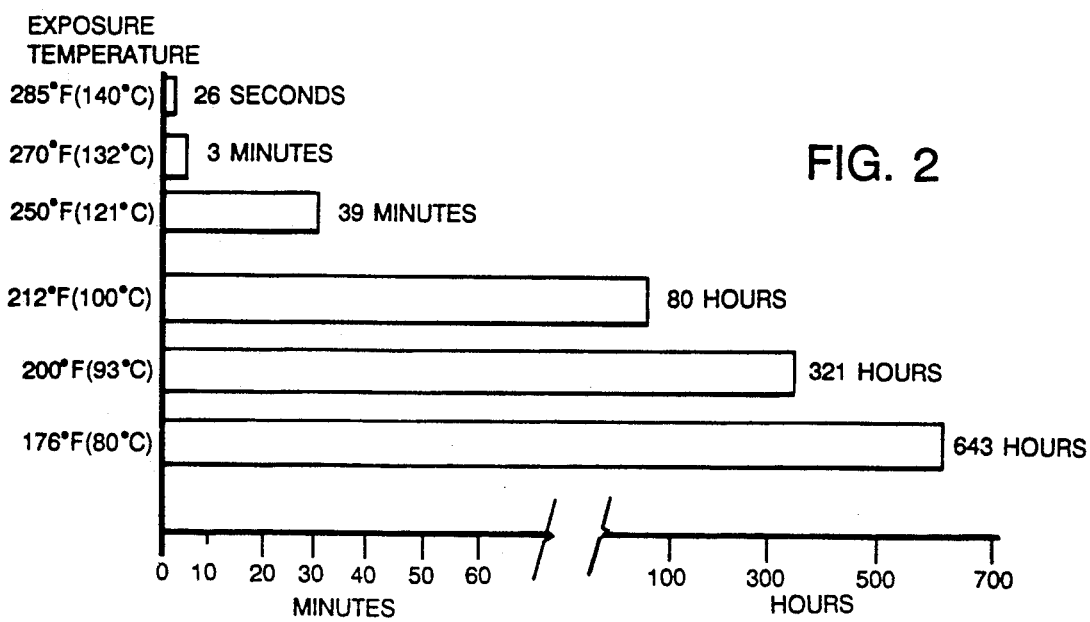
FIG. 2 is a residence time/exposure temperature chart.

The interrelationship between the residence time and temperature is shown in FIG. 2. Referring to FIG. 2, a time/temperature chart indicates the necessary temperatures and associated residence times to achieve sterilization, as sterilization is defined by Favero and Bond. For instance, a waste particle must remain in the disinfection system of FIG. 1 for 3 minutes if the temperature in the disinfection system is 270° F. At this particular temperature, a residence time of less than 3 minutes will not result in adequate sterilization as it is defined by Favero and Bond.

A computer control system (not shown), for controlling all aspects of the closed system's operation, controls the residence time and the temperature. The computer control system controls the residence time by causing the shredders and the screw conveyors to slow down or speed up their rate of operation. Again, the time/temperature chart of FIG. 2 indicates the required residence times for several selected temperatures.

Referring back to FIG. 1, air is continuously drawn through the system by fan 32. The continuous action of the fan serves to reduce the pressure in the closed system (i.e., create negative pressure), direct any airborne contaminants in the closed system to the filters 28, 30, and prevent any emissions from escaping the closed system and entering the facility or room in which the closed system is located. The continuously moving air keeps the pressure in the closed system at near atmospheric pressure, and therefore the disinfection system 22 need not be a pressure vessel. The operational pressure range for the disinfection system is approximately 10 to 20 psia. This relatively low operational pressure range allows a relatively inexpensive disinfection system to be used, and therefore results in a less costly overall closed system, as compared to what the cost would be if a pressure vessel were required.

The continuously drawn air also withdraws any vaporized moisture coming off of the waste particles as they are heated and keeps the moisture in the closed system below the dew point to prevent condensate from forming in the system. Vaporized moisture is often created during the indirect heating of the waste because the waste typically has an inherent moisture content of anywhere from zero to fifty percent. The continuous action of the fan draws air over the waste to help remove this vaporized moisture. As shown in FIG. 1, the fan draws air from the shredder section 16 (line 88), the hold-up and disengagement chamber 24 (line 90), and disinfection system 22 (line 96) into the dual filtration system 28, 30. The filtered air exiting the fan, and therefore the closed system, is an environmentally clean discharge.

The computer control system (not shown) mentioned previously also controls the air flow such that a desired closed system pressure and waste material moisture content is maintained, and such that moisture in the closed system is kept below the dew point to prevent condensate from forming in the closed system. Typically, the computer control system acts to keep the moisture content of the waste material below five percent during processing.

The processed (i.e., destroyed and treated) waste that exits the disinfection system at outlet end 84 is dropped into the hold-up and disengagement chamber 24. It then passes through air lock 26 and is deposited into a compactor/trailer system 92 for easy hauling to a landfill or a "waste-to-energy" facility. The compactor/trailer system is capable of compacting the processed waste to reduce its volume.

A system shutdown (for whatever reason) results in steam being injected, by emergency steam injectors 94, directly onto any waste contained in the disinfection system 22, the infeed chamber 14, and the shredder section 16. In a shutdown, any waste left in the closed system has probably not been adequately processed (i.e., destroyed and treated), and therefore it is necessary to somehow disinfect it before any maintenance work is attempted. The steam generator 86 provides the "emergency steam" necessary to achieve the disinfection. The steam is applied for a sufficient period of time, usually approximately one to two hours, such that the infectious waste left in the closed system is properly disinfected. Also, a pressure sufficient to prevent condensate from forming is maintained in the closed system during this period of time. The steam then condenses, is drained off, and discharged into the sewer, possibly along with chemical treatment using chlorine, bleach, or hypochlorite solution to ensure the discharge is disinfected. The closed system may now be safely dismantled and the waste removed. If repairs do not require dismantling of the closed system, the system may be simply restarted without removing the enclosed waste. In this latter case, the waste will just continue through the system.

It is important to realize that the computer control system (not shown) controls all aspects of the closed system's operation. Specifically, it controls the start-up and shutdown of the entire system as well as the infeed conveyor rate, steam temperature, waste temperature, flow of air, shredder rate, screw conveyor rate, pressure in the closed system, etc. However, manual overrides for all settings are also provided.

An obvious advantage of the closed system just described is that it satisfies the EPA requirements of treatment and destruction of infectious medical waste. Other advantages of the closed system include its ability to achieve high levels of disinfection (i.e., its ability to achieve sterilization as defined by Favero and Bond) and its ability to maximize heat transfer to the waste by increasing the surface area of the waste that is exposed to the heat (i.e., by shredding the waste into small particles). Still other advantages include the low cost of operation that results from the continuous processing of the waste and the relatively low amount of energy required to process each pound of waste. The relatively high temperatures achievable by the closed system are another advantage. Also, the closed system does not create the extremely foul odors that normally result in systems that rely solely on the direct application of steam (or a chemical) to the medical waste. Furthermore, no potentially environmentally harmful effluent is discharged into either the atmosphere or the public sewer in normal operation.

Figure 3:
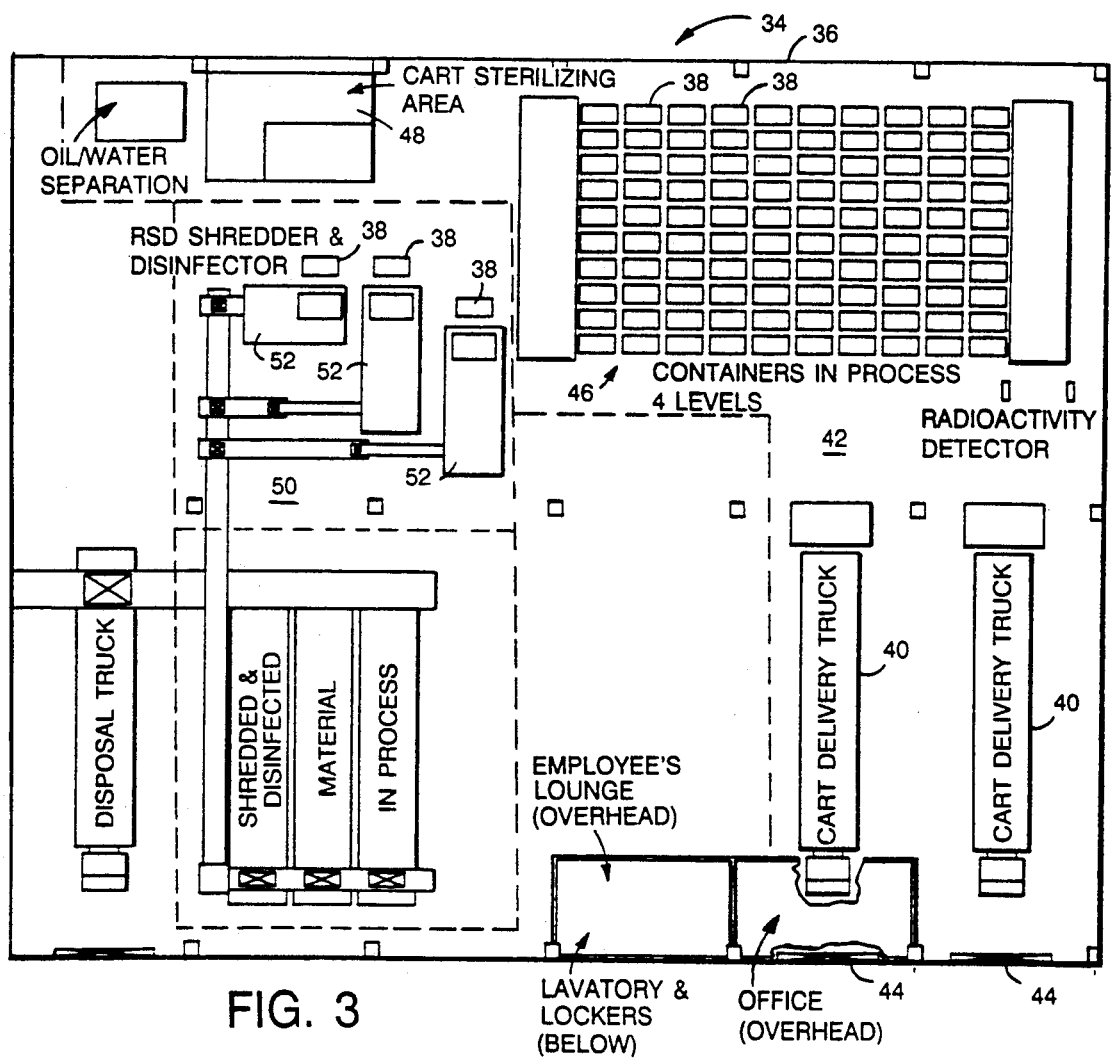
FIG. 3 is a plan view of a facility for receiving large amounts of medical waste and for processing the waste by using the closed system of FIG. 1.

Referring to FIG. 3, a facility 34, housed in a building 36, that receives large amounts of medical waste may use one or more of the closed systems (FIG. 1) for processing the waste. Infectious or red bag waste is collected and transported to facility 34 via an integrated transportation system built around a standard rigid, sealable container 38 (e.g., a box, drum, or barrel). Each sealed container contains between twenty-five and thirty pounds of red bag waste and can be easily handled by workers at both ends of the journey. The containers are sealed at the source and transported in trucks 40 used solely for this purpose. The waste in each container is traced with an automated manifest system so that waste generator facilities will have a continuous record of the safe disposal of each load sent to the facility.

Receiving systems 42 in the front end of facility 34 are designed for receiving and unloading containers 38. Typically, facility 34 has the capacity to process from twenty-four to one hundred tons of medical waste per day (24-100 TPD), the equivalent of approximately five to seven delivery trucks 40 containing sealed containers of medical waste. Delivery trucks 40 drive through doors 44 into building 36 where the containers 38 are unloaded from the trucks and sent to a holding area 46. Even though the red bag waste contained in the containers is sealed in bags or boxes designed specifically for medical waste, the containers are cleaned after usage, as a precautionary measure, in a container sterilizing area 48. Cleaned and sterilized containers are reloaded on the delivery trucks and returned to the waste generation facilities where they are reloaded with red bag medical waste requiring disposal.

A waste destruction and treatment portion 50 of facility 34 may include one or more of the closed systems of FIG. 1. Still referring to FIG. 3, sealed containers of medical waste are brought one by one to the closed systems 52. Typically, the waste destruction and treatment portion 50 of facility 34 operates for sufficient hours each day such that all received red bag medical waste is treated and destroyed within 24 hours of being received.

Each container 38 is unsealed, lifted, and emptied onto the infeed conveyor of the closed system by a lifting mechanism (not shown) which attaches to the container. Empty containers are conveyed to container cleaning and sterilizing area 48 and then into inventory, ready to be sent out again.

Figure 4A:
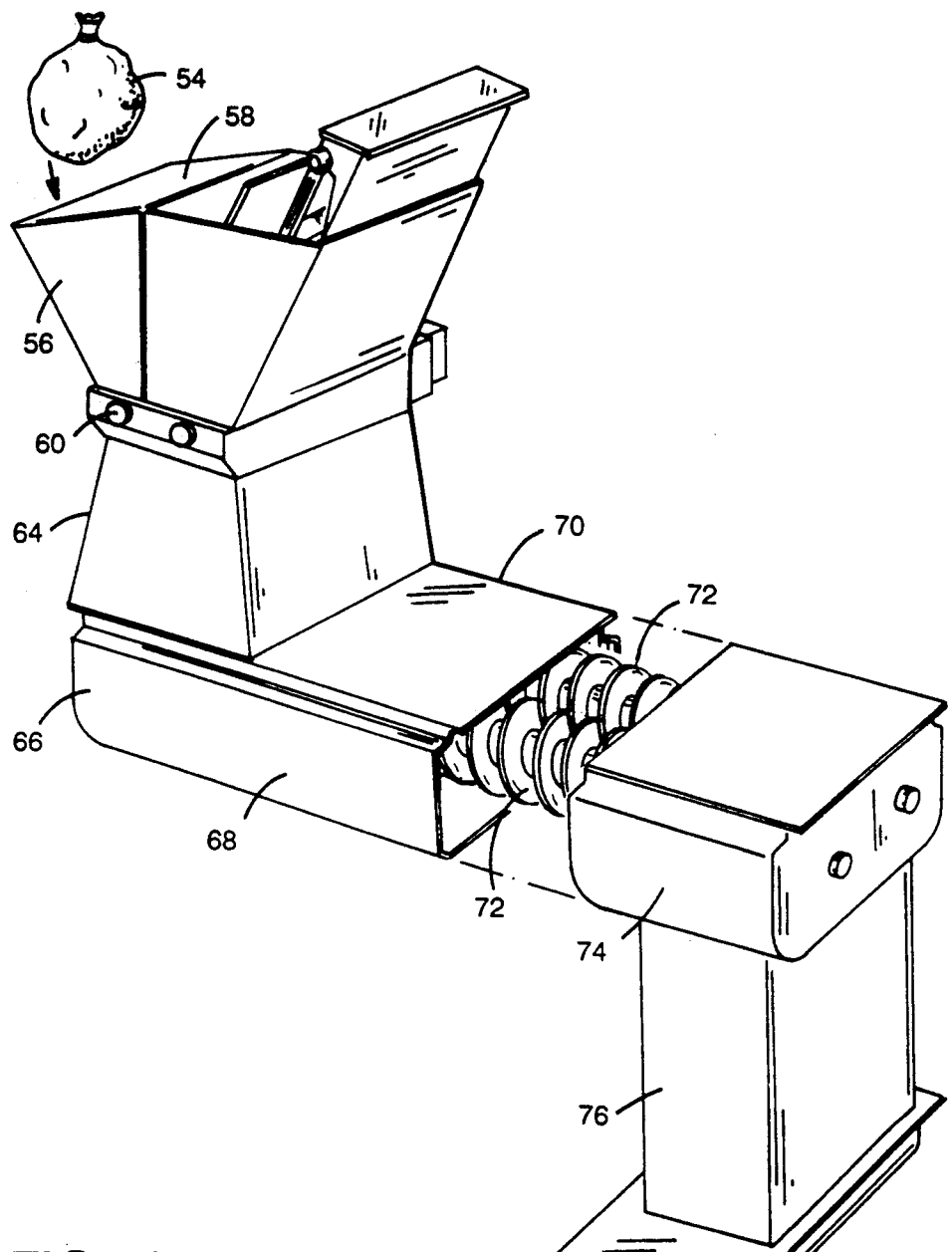
FIGS. 4(a) and 4(b) are perspective views of an embodiment of a portion of the closed system of FIG. 1.
Figure 4B:
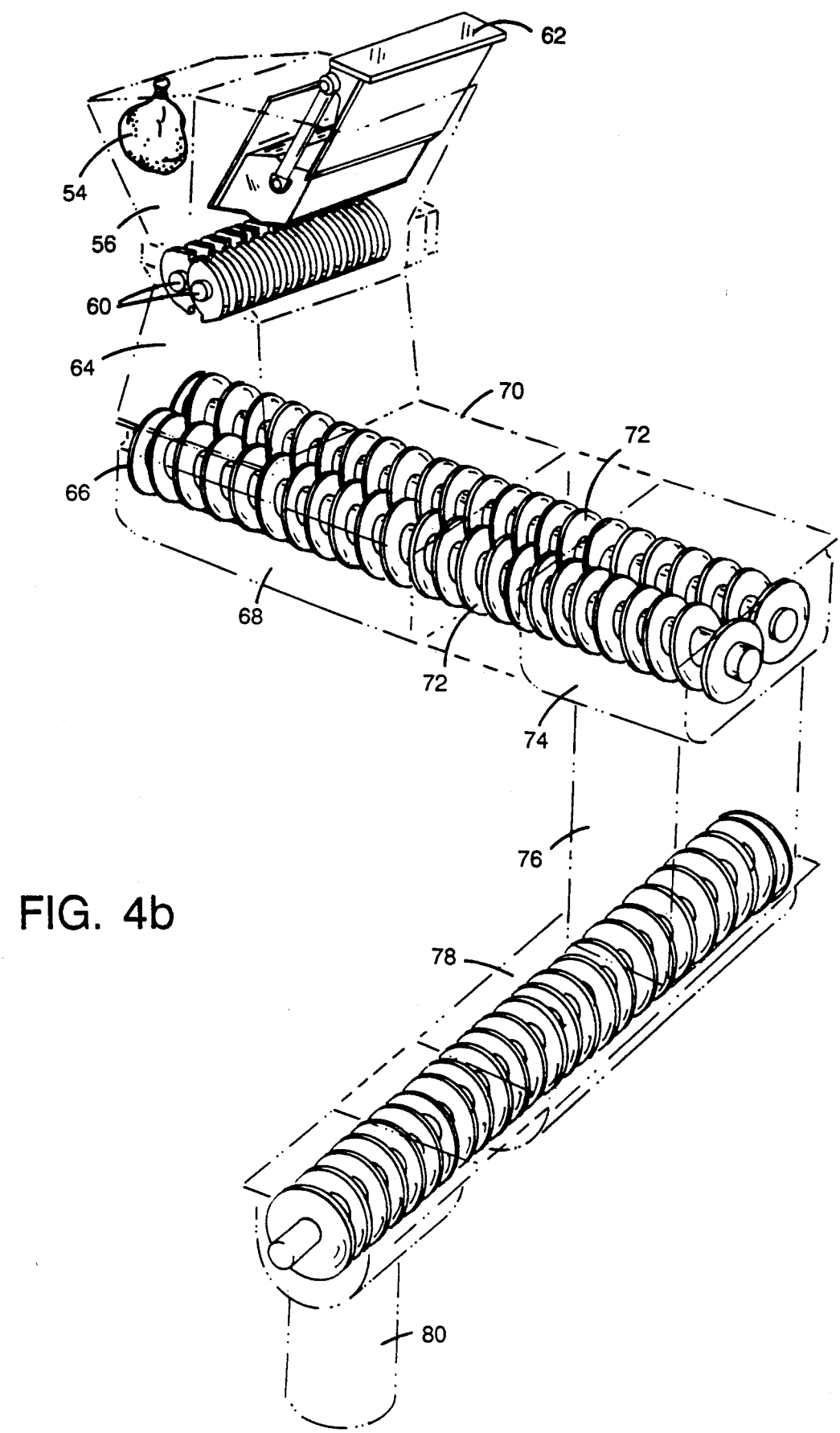

A particular embodiment of a portion of the closed system of FIG. 1 is shown in FIGS. 4(a) and 4(b), where FIG. 4(b) shows outer surfaces in phantom. In this embodiment, the red bag medical waste 54 enters into a hopper 56 and a surge feed hopper door 58, preferably operated by a hydraulic lift, seals the hopper once waste has been fed into it. Hopper 56 feeds a shredder assembly 60 which destroys the red bag medical waste 54 by reducing it to granules having a maximum dimension of 3 inches. A pneumatic or hydraulic ram 62 operates to help force the waste through shredder assembly 60. A hopper/shredder assembly and ram of the type described is commercially available as Model No. 1000-E from Shredding Systems, Inc. (28655 SW. Boones Ferry Rd., Wilsonville, Oreg. 97070), the specification of which is incorporated herein by reference. Similar equipment is also commercially available from Shred Pax Corp. (136 West Commercial Ave., Wooddale, Ill. 60191).

The output stream of shredder assembly 60 consists of granulated waste which passes into a surge hopper 64 which feeds the input end 66 of a sealed disinfection processor 68, such as that manufactured by Denver Equipment Co. (621 South Sierra Madre, Colorado Springs, Colo. 80901) . Disinfection processor 68 includes a sealed trough 70 containing two interleaved counter-rotatable hollow screw conveyors 72 which transport the granulated waste from the input end 66 of the disinfection processor to the output end 74. Oil or steam is circulated within each of the hollow screws to indirectly heat, and thereby treat, the granulated waste as it travels the length of the disinfection trough. A hollow screw processor of this type is commercially available as Holo-Flite ® Processor No. 1D2424-6 from Denver Equipment Co. (621 South Sierra Madre, Colorado Springs, Colo. 80901), the specification of which is incorporated herein by reference. Similar equipment is also commercially available from Therm-A-Core, Inc. (44533 Grimmer Blvd., Fremont, Calif. 94538) and Bethlehem Corp.

As described previously, a system shutdown would result in steam being injected directly into both the trough 70 of the sealed disinfection processor 68 (i.e., the volume surrounding the hollow screws) and the hopper 56 in order to treat any infectious waste left in the system during the shutdown. In the case of a shutdown, the pressure and temperature inside the trough are controlled and maintained for a sufficient period of time (approximately one to two hours) such that condensate is prevented from being formed and the infectious waste left in the system is properly disinfected. The steam is then allowed to condense, drained off, and discharged into the sewer, possibly along with chemicals to ensure the discharge is disinfected. If the system needs to be dismantled to be repaired, the waste left in the system can now be removed safely. Alternatively, if repairs do not require dismantling of the system, the system may be simply restarted after repairs are made.

The disinfection processor discharges the treated and destroyed granulated waste into a discharge surge hopper 76 which directs the waste to a conventional discharge screw conveyor 78, which then discharges the waste through outlet 80.

Other embodiments are within the following claims.

For example, hot gas or hot oil may be circulated through the hollow screw conveyors instead of steam.

A single hollow screw conveyor may be used instead of two interleaved counter-rotatable hollow screw conveyors. Also, other types of indirect-heat-exchangers besides the screw conveyors could be used.

A single shredder could be used in place of two in series with each other. Also, adequate destruction of the waste could be achieved by other types of machines besides shredders. For instance, hammer mills, pulverizers, grinders, etc. could be used. Moreover, any number and combination of low speed shear shredders, hammer mills, pulverizers, grinders, etc. could be used.

The infeed conveyor 12 (FIG. 1) can include a continuous weighing system.

An ordinary dumpster or any other collection means can be used instead of the compactor/trailer system 92 (FIG. 1). Also, the processed waste exiting from the closed system could be input directly into a "waste-to-energy" facility as fuel.

Instead of injecting steam into the closed system upon a system shutdown, bleach, chlorine, or hypochlorite solution could be injected to disinfect any waste left in the system.

The closed system may be configured as a self-contained mobile disinfection unit, or as an integrated unit which is part of a medical facility that produces red bag waste or a regional collection center that collects red bag waste from various sources.

Although it is not the preferred mode of operation, it is possible to use direct heating alone to disinfect the waste. In such a mode of operation, steam at 212° to 350° F. would be injected directly into the closed system and the system would be operated under a pressure (e.g., 15 to 250 psig) sufficient to prevent condensate from forming. Of course, in this case, disinfection system 22 (FIG. 1) would have to be a pressure vessel, which would significantly increase the cost and complexity of the closed system.

What is claimed is:

1. A method for disposing of infectious medical waste in a closed system, comprising the steps of shredding said waste in said closed system to reduce the waste to small particles; and indirectly heating said waste particles in said closed system by contacting said waste particles with a heated surface, said indirect heating being to a sufficiently high temperature and for a sufficient period of time to produce a quantitative assurance of sterilization of said waste particles, said indirect heating step utilizing a pair of hollow screw conveyors which are interleaved and counter-rotatable, and said indirect heating step comprising transporting said waste particles from one end of said hollow screw conveyors to the other end of said hollow screw conveyors, said hollow screw conveyors having outside surfaces being adapted to accept a heat conducting medium inside said hollow sections so that said heat conducting medium heats said outside surfaces, whereby said waste particles contacting said outside surfaces are heated indirectly by said heat conducting medium;

wherein air is continuously drawn through said closed system to control the pressure and moisture in said closed system.

2. The method of claim 1 wherein said shredding and indirect heating steps are carried out without the addition of any liquid.

3. The method of claim 1 wherein said shredding step comprises shredding said waste into particles with no dimension greater than approximately one inch.

4. The method of claim 1 wherein said indirect heating step comprises indirectly heating said waste particles to at least 220 degrees Fahrenheit.

5. The method of claim 1 wherein said heat conducting medium comprises heated oil.

6. The method of claim 1 wherein said heat conducting medium comprises a heated gas.

7. The method of claim 1 wherein said heat conducting medium comprises steam.

8. The method of claim 7 wherein said steam is superheated.

9. The method of claim 7 wherein said steam is saturated.

10. The method of claim 1 further comprising the step of filtering said continuously drawn air before it is discharged into the atmosphere.

11. The method of claim 10 wherein said filtering step comprises filtering with both an activated carbon filter to remove volatile organics from the air and a high efficiency particulate air (HEPA) filter to remove submicron particles, including bacteria, from the air.

12. A closed system for disposing of infectious medical waste, comprising a shredder for shredding said waste and reducing said waste to small particles;

a disinfection unit, connected to said shredder via a gas-solid separator mechanism, for disinfecting said shredded waste by indirectly heating said waste particles, said disinfection unit comprising a heated surface capable of indirectly heating said waste particles contacting said surface to a sufficiently high temperature and for a sufficient period of time to produce a quantitative assurance of sterilization of said waste particles, said disinfection unit further comprising a pair of hollow screw conveyors which are interleaved and counter-rotatable, said hollow screw conveyors contacting and transporting said waste particles from one end of said unit to the other end, said hollow screw conveyors having outside surfaces and being adapted to accept a heat conducting medium inside said hollow sections so that said heat conducting medium heats said outside surfaces, whereby said waste particles contacting said outside surfaces are heated indirectly by said heat conducting medium;

wherein air is continuously drawn through said closed system to control the pressure and moisture in said closed system.

13. The closed system of claim 12 wherein no liquid is added to said system.

14. The closed system of claim 12 wherein said shredder produces particles with no dimension greater than approximately one inch.

15. The closed system of claim 12 wherein said disinfection unit indirectly heats said waste particles to at least 220 degrees Fahrenheit.

16. The closed system of claim 12 wherein said heat conducting medium comprises heated oil.

17. The closed system of claim 12 wherein said heat conducting medium comprises a heated gas.

18. The closed system of claim 12 wherein said that conducting medium comprises steam.

19. The closed system of claim 18 wherein said steam is superheated.

20. The closed system of claim 18 wherein said steam is saturated.

21. The closed system of claim 12 further comprising a filtration unit for filtering said continuously drawn air before it is discharged into the atmosphere.

22. The closed system of claim 21 wherein said filtration unit comprises both an activated carbon filter for removing volatile organics in the air and a high efficiency particulate air (HEPA) filter for removing submicron particles, including bacteria, in the air.

* * * * *

UNITED STATES PATENT AND TRADEMARK OFFICE
CERTIFICATE OF CORRECTION

PATENT NO.   : 5,277,136

DATED        : January 11, 1994

INVENTOR(S)  : Robert S. Davis

It is certified that error appears in the above-identified patent and that said Letters Patent is hereby corrected as shown below:

Column 3, line 16, replace "o the", with --of the--;

Column 4, line 13, after "system", insert --22--;

Column 4, line 14, replace "with the 26 seconds to" with --with the range 26 seconds to--;

Column 4, line 57, delete "often";

Column 10, claim 18, line 16, replace "that" with --heat--.

Signed and Sealed this

Seventh Day of June, 1994

Attest:

BRUCE LEHMAN

Attesting Officer        Commissioner of Patents and Trademarks

UNITED STATES PATENT AND TRADEMARK OFFICE
CERTIFICATE OF CORRECTION

PATENT NO. : 5,277,136
DATED : January 11, 1994
INVENTOR(S) : Robert S. Davis

It is certified that error appears in the above-indentified patent and that said Letters Patent is hereby corrected as shown below:

Title page, item [73], Assignee:  should read -- B&B Joint Venture--.

Signed and Sealed this

Ninth Day of August, 1994

Attest:

BRUCE LEHMAN

*Attesting Officer*   *Commissioner of Patents and Trademarks*